(12) United States Patent
Shi et al.

(10) Patent No.: US 9,897,593 B2
(45) Date of Patent: Feb. 20, 2018

(54) SYSTEMS AND METHODS FOR AUTOMATED HANDLING OF LIVE ORGANISMS

(71) Applicant: CITY UNIVERSITY OF HONG KONG, Kowloon Tong (HK)

(72) Inventors: Peng Shi, Guangdong (CN); Xudong Lin, Guangdong (CN)

(73) Assignee: City University of Hong Kong, Hong Kong (HK)

( * ) Notice: Subject to any disclaimer, the term of this patent is extended or adjusted under 35 U.S.C. 154(b) by 237 days.

(21) Appl. No.: 14/705,128

(22) Filed: May 6, 2015

(65) Prior Publication Data

US 2016/0327545 A1 Nov. 10, 2016

(51) Int. Cl.
*G01N 33/50* (2006.01)
*B01L 3/00* (2006.01)

(52) U.S. Cl.
CPC .... *G01N 33/5088* (2013.01); *B01L 3/502761* (2013.01); *B01L 3/5025* (2013.01); *B01L 2200/0663* (2013.01); *B01L 2200/0668* (2013.01); *B01L 2300/0816* (2013.01); *B01L 2300/0864* (2013.01); *B01L 2400/0487* (2013.01); *G01N 2333/4603* (2013.01)

(58) Field of Classification Search
CPC ..................... G01N 33/5088; B01L 3/502761
USPC .......................................................... 506/9
See application file for complete search history.

(56) References Cited

U.S. PATENT DOCUMENTS

2007/0207450 A1\* 9/2007 Rodgers ............... B01J 19/0046
435/3

OTHER PUBLICATIONS

Zhu et al., Cytometry Part A, Nov. 2014, pp. 921-932.\*
Wang et al., Biosensors and Bioelectronics 48, 2013, pp. 188-196.\*
Francisco Varela et al., The Brainweb: Phase Synchronization and Large-Scale Integration, Nature Reviews, Neuroscience, vol. 2, Apr. 2001, pp. 229-239.
Eric R. Kandel et al., Principles of Neural Science, Fifth Edition, Acta Endocrinologica (Buc), vol. X, No. 3, p. 529, 2014.
Daniel Huber et al., Sparse Optical Microstimulation in Barrel Cortex Drives Learned Behaviour in Freely Moving Mice, Nature Letters, vol. 451, Jan. 3, 2008, pp. 61-64.
A. Paul Alivisatos et al., The Brain Activity Map Project and the Challenge of Functional Connectomics, Neuron, NeuroView, vol. 74, Jun. 21, 2012, pp. 970-974.
Eric R. Kandel et al., Neuroscience Thinks Big (and Collaboratively), Nature Reviews, Neuroscience, vol. 14, Sep. 2013, pp. 659-664.
Masao Imaizumi et al., Brain and Whole-Body Imaging in Nonhuman Primates of [$^{11}$C]PBR28, a Promising PET Radioligand for Peripheral Benzodiazepine Receptors, NeuroImage, vol. 39, 2008, pp. 1289-1298.
Richard G. Wise, PhD et al., The Role of fMRI in Drug Discovery, Journal of Magnetic Resonance Imaging, 2006, pp. 862-876.
Tina Schrödel et al., Brain-Wide 3D Imaging of Neuronal Activity in *Caenorhabditis elegans* with Sculpted Light, Nature Methods, vol. 10, No. 10, Oct. 2013, pp. 1013-1020.
Jing W. Wang et al., Two-Photon Calcium Imaging Reveals an Odor-Evoked Map of Activity in the Fly Brain, Cell, vol. 112, pp. 271-282, Jan. 24, 2003.
Raju Tomer et al., Quantitative High-Speed Imaging of Entire Developing Embryos with Simultaneous Multiview Light-Sheet Microscopy, Nature Methods, vol. 9, No. 7, Jul. 2012, pp. 755-763.
Misha B. Ahrens et al., Brian-Wide Neuronal Dynamics During Motor Adaptation in Zebrafish, Nature, vol. 485, May 24, 2012, pp. 471-477.
Jerry L. Chen et al., Imaging Neuronal Populations in Behaving Rodents: Paradigms for Studying Neural Circuits Underlying Behavior in the Mammalian Cortex, The Journal of Neuroscience, Nov. 6, 2013, pp. 17631-17640.
Misha B. Ahrens et al., Whole-Brain Functional Imaging at Cellular Resolution Using Light-Sheet Microscopy, Nature Methods, vol. 10, No. 5, May 2013, pp. 413-420.
Paul Goldsmith, Zebrafish as a Pharmacological Tool: the How, Why and When, Current Opinion in Pharmacology, vol. 4, Issue 5, Oct. 2004, pp. 504-512.
Leonard I. Zon et al., In Vivo Drug Discovery in the Zebrafish, Nature Reviews, vol. 4, Jan. 2005, pp. 35-44.
Carlos Pardo-Martin et al., High-Throughput In Vivo Vertebrate Screening, Nature Methods, vol. 7, No. 8, Aug. 2010, pp. 634-636.
Wei-Heong Tan et al., A Trap-and-Release Integrated Microfluidic System for Dynamic Microarray Applications, PNAS, vol. 104, No. 4, Jan. 23, 2007, pp. 1146-1151.
Stefan Kobel et al., Optimization of Microfluidic Single Cell Trapping for Long-Term On-Chip Culture, Lab on a Chip, vol. 10, 2010, pp. 857-863.
Weiwei Shi et al., Droplet-Based Microfluidic System for Individual *Caenorhabditis elegans* Assay, Lab on a Chip, vol. 8, 2008, pp. 1432-1435.
Kwanghun Chung et al., A Microfluidic Array for Large-Scale Ordering and Orientation of Embryos, Nature Methods, vol. 8, No. 2, Feb. 11, pp. 171-176.
Philippe Thévenaz et al., A Pyramid Approach to Subpixel Registration Based on Intensity, IEEE Transactions on Image Processing, vol. 7, No. 1, Jan. 1998, pp. 27-41.

(Continued)

*Primary Examiner* — Karla A Dines
(74) *Attorney, Agent, or Firm* — Heslin, Rothenberg, Farley & Mesiti, P.C.

(57) ABSTRACT

There is provided a system for automated handling of live organisms for studying biological development of the organisms. The system has a reservoir for containing a plurality of the organisms, a module for automatically trapping and orienting the organisms in desired positions for imaging purpose, a module for automatically controlling orientation of the organisms leaving the reservoir and entering the trapping and orienting module, and a module for automatically loading the organisms from the reservoir into the orientation control module. The trapping and orienting module may include an array of channels configured to allow flow of fluid and travel of the organisms in the system.

20 Claims, 9 Drawing Sheets
(9 of 9 Drawing Sheet(s) Filed in Color)

(56) References Cited

OTHER PUBLICATIONS

Brian S. Meldrum, Glutamate as a Neurotransmitter in the Brain: Review of Physiology and Pathology, The Journal of Nutrition, 2000, pp. 1007S-1015S.

Richard J. Lewis et al., Therapeutic Potential of Venom Peptides, Nature Reviews, vol. 2, Oct. 2003, pp. 1-13.

David J. Craik et al., Chemical Modification of Conotoxins to Improve Stability and Activity, ACS Chemical Biology, vol. 2, No. 7, 2007, pp. 457-468.

Heinrich Terlau et al., *Conus* Venoms: A Rich Source of Novel Ion Channel-Targeted Peptides, Physiol. Rev., 2004, pp. 41-68.

G.P. Miljanich, Ziconotide: Neuronal Calcium Channel Blocker for Treating Severe Chronic Pain, Current Medicinal Chemistry, vol. 11, 2004, pp. 3029-3040.

Julie A. Haack et al., A γ-Carboxyglutamate Containing Peptide with N-Methyl-$_D$-Aspartate Antagonist Activity, The Journal of Biological Chemistry, vol. 265, No. 11m Apr. 15, 1990, pp. 6025-6029.

Zhenyu Sheng et al., Subtype-Selective Antagonism of N-Methyl-D-Aspartate Receptor Ion Channels by Synthetic Conantokin Peptides, National Institute of Health Public Access, Neuropharmacology, Jul. 2007, pp. 1-25.

Laetitia Mony et al., Allosteric Modulators of NR2B-Containing NMDA Receptors: Molecular Mechanism and Therapeutic Potential, British Journal of Pharmacology, Jul. 8, 2009, pp. 1301-1317.

Richard White et al., Zebrafish Cancer: The State of the Art and the Path Forward, Nature, vol. 13, Sep. 2013, pp. 624-636.

Chris H. Polman et al., A Randomized, Placebo-Controlled Trial of Natalizumab for Relapsing Multiple Sclerosis, The New England Journal of Medicine, vol. 354, No. 9, Mar. 2, 2006, pp. 899-910.

Gary Walsh, Biopharmaceutical Benchmarks 2010, Nature Biotechnology, vol. 28, No. 9, Sep. 2010, pp. 917-924.

Diana X. Yu et al., Therapeutic Translation of iPSCs for Treating Neurological Disease, Cell Stem Cell, vol. 12, Jun. 6, 2013, pp. 678-688.

Mary Ann Mascelli, PhD et al., Molecular, Biologic, and Pharmacokinetic Properties of Monoclonal Antibodies: Impact of These Parameters on Early Clinical Development, Journal of Clinical Pharmacology, 2007, pp. 553-565.

Bai Lu et al., BDNF-Based Synaptic Repair as a Disease-Modifying Strategy for Neurodegenerative Diseases, Nature Reviews, Neuroscience, vol. 14, Jun. 2013, pp. 401-416.

Anna Kaufmann et al., Multilayer Mounting Enables Long-Term Imaging of Zebrafish Development in a Light Sheet Microscope, Research Report, Technical Paper, 2012, pp. 3242-3247.

Lauren L. Bischel et al., Zebrafish Entrapment by Restriction Array (ZEBRA) Device: a Low-Cost, Agarose-Free Zebrafish Mounting Technique for Automated Imaging, Lab on a Chip, vol. 13, 2013, pp. 1732-1736.

Donald T. Frazier et al., Tricaine (MS-222): Effects on Ionic Conductances of Squid Axon Membranes, European Journal of Pharmacology, vol. 33, Issue 2, Sep.-Oct. 1975, 1 page (Abstract Only).

Brian S. Muntean et al., A Comparative Study of Embedded and Anesthetized Zebrafish In Vivo on Myocardiac Calcium Oscillation and Heart Muscle Contraction, Frontiers in Pharmacology, vol. 1, Article 139, Dec. 2010, pp. 1-9.

Christine Grienberger et al., Imaging Calcium in Neurons, Neuron, vol. 73, Mar. 8, 2012, pp. 862-885.

Michelle Vincler et al., Molecular Mechanism for Analgesia Involving Specific Antagonism of α9α10 Nicotinic Acetylcholine Receptors, PNAS, vol. 103, No. 47, Nov. 21, 2006, pp. 17880-17884.

\* cited by examiner

SYSTEMS AND METHODS FOR AUTOMATED HANDLING OF LIVE ORGANISMS

FIELD OF THE INVENTION

The present invention is concerned with systems and methods for automated handling of live organisms such as vertebrate larvae, for example for use in studying biological development or morphology of organism

BACKGROUND OF THE INVENTION

Small vertebrate animals such as zebrafish are increasingly used at various stages of drug discovery process and becoming a useful and cost-effective alternative to mammalian models (such as rodents, dogs and pigs). Specific advantages of zebrafish, including a high degree of conservation to mammals, optically transparent organs, rapid development, and easy genetic manipulation process, make it one of the ideal models for high-throughput screening in living animals, which had previously been limited to invertebrates such as flies, worms and yeast. Moreover, zebrafish models have shown their desirable attributes on a huge scale of studies, including pharmaceutical development, genetic studies, and identification of the cellular targets of new compounds.

However, most studies involving organ-specific imaging of zebrafish require manual manipulation and orientation of fish larvae. Early screening methods for Zebrafish model were multi-well plate based, where fish embryos were manipulated and imaged inside each isolated compartment. Such screens have been used to study drug-induced toxicity to analyze hepatotoxicity, cardiotoxicity, and neurotoxicity. Advances in microscopy and image processing technique have also enabled behavioral assays on larvae within microwells. However, there are several limitations for such multi-well plate based methods. First, consistent long-term visualization of key organs in zebrafish is not possible within the wells, given their random orientation and fast movement. Second, even though the fishes can be anesthetized to minimize any significant body movement, the procedure is manual and laborious. Third, it is simply impossible to perform real-time organ specific activity monitoring during acute drug treatment using the multi-well based approach. These limitations have motivated development of newer tools that can enable handling the animals on other platforms.

Progress were made by some companies and academic labs. Pardo-Martin et al developed a platform capable of performing cellular-resolution imaging of zebrafish larvae at any orientation, which are automatically loaded larvae from multi-well plates and placed inside glass capillaries. While the system is mostly automated, this capillary-based platform only process very limited number of animals, and still requires anesthetic treatment to fishes, which may interfere with regular physiological functions, especially in the brain. In addition, there is no extra orthogonal dimension for coupling any drug treatment due to the complete encapsulation of fish larva in a capillary, and thus is not suitable for studies involve acute drug testing. An automated microfluidic device demonstrated by Chunhong Zheng et al aims to study drug dynamics in vivo using zebrafish model. However, this platform cannot be used to study specific organs with cellular level resolution due to the lack of orientation control.

The present invention seeks to provide a system which mitigates problems of existing systems for high-throughput studies involving small vertebrate animals such as zebrafish, or at least to provide an alternative to the public.

SUMMARY OF THE INVENTION

According to a first aspect of the present invention, there is provided a system for automated handling of live organisms for studying biological development of the organisms, comprising:
  a) a reservoir for containing a plurality of the organisms;
  b) a module for automatically trapping the organisms in desired positions for imaging purpose;
  c) a module for automatically orientating the organisms with desired angels for imaging purpose;
  d) a module for automatically controlling head-to-tail direction of the organisms leaving the reservoir and entering the trapping and orientating module; and
  e) a module for automatically loading the organisms from the reservoir into the trapping and orientation control module;
  wherein the trapping and orientating module includes an array of fluidic channels configured to allow flow of fluid and travel of the organisms in the system, the array of channels having:
  i) a first conduit arranged generally horizontally and to which the oriented organisms are introduced;
  ii) one or more second conduits arranged generally vertically or perpendicularly with respect to the first conduit, the second conduit or conduits connected to and branched off from the first conduit and adapted to trap one organism in each vertical conduit; and
  iii) a third conduit arranged adjacent and connected to the first conduit, the third conduit is configured such that fluid can be ejected from the third conduit to the first conduit via a shunt connecting the third and first conduits, deflecting fluid flow in the first conduit to the second conduit.

Preferably, the organisms may be teleost. More preferably, the teleost may be zebrafish larvae. In some embodiments, the system may be configured to study different organs of the organism, including heart, liver, vascular structure, etc.

Advantageously, the system may be free of using anesthetic or gel in immobilizing the organisms. Without the use of anesthetic or gel, the organisms would be least affected and the reliability of results from studying of the organisms using the system is much increased.

In an embodiment, the system may comprise a first inlet via which the organisms are introduced into the array of channels, and a second inlet configured to allow an increase in hydrodynamic flow into the second conduit.

The system may comprise a plurality of pairs of the second conduits and corresponding shunts, the shunts configured to deflect the fluid flow in the first conduit to the second conduits, respectively, the conduits defining a capillary circuitry.

The system may comprise a detection unit and a valve unit for discriminating and switching direction in a fluidic circuitry. The fluidic circuitry may be a loop capillary fluid circuitry. The detection unit may be a photo-detection unit including an illumination means and a camera configured to identify orientation of a larva leaving the reservoir for the first conduit. The illumination means may be in the form of LED.

The first conduit may have an internal width of substantially 800 μm.

The second conduit may resemble an elongate funnel structure having an enlarged portion at an inlet end, a restricted portion at an outlet end opposite to the inlet end, and a neck portion therebetween. The enlarged inlet portion may be configured to transition to the restricted outlet portion sharply at the neck portion inlet end. The neck portion inlet end may have an internal width of substantially 150 μm.

The second conduit may have a length of substantially 9 mm, the inlet may have an internal width of substantially 2.1 mm, the outlet has an internal width of substantially 100 μm.

The second conduit may be configured to trap a zebrafish larva at a development stage of 2-4 days, 4-6 days, or 6-8 days of post fertilization. The second conduit may be configured to trap a zebrafish larva in its lateral position. The height of the second conduit may be substantially 150 μm. The second conduit may be configured to trap a zebrafish larva in its dorsal position. The height of the second conduit may be substantially 500 μm. The third conduit may have an internal width of substantially 500-800 μm. The shunt may have an internal width and a length both of substantially 400-500 μm.

Suitably, the first conduit may have an inlet and an outlet, and is subjected to a positive fluid pressure in operation.

In a preferred embodiment, the system may be configured to provide a stimulus to the zebrafish larva trapped in the second conduits.

Suitably, the system may be made of essentially a transparent material suitable for optical stimulus or reception.

In one embodiment, the system may comprise at least one syringe pump for loading larva into the capillary fluidic circuitry and one or more fluidic valves for controlling operation state in the conduits. The syringe pump may be coupled the orientation module and the fluid valve(s).

The system may comprise a computer unit for controlling flow rate in the first, second and third conduits, and performing automated control of larva loading cycles.

According to a second aspect of the present invention, there is provided a method for high-throughput screening of subject whole organism, comprising:
a) automatically loading the organisms from a reservoir into a fluidic circuitry;
b) automatically switching head-to tail orientation of the organisms;
c) automatically trapping the organisms; and
d) automatically orientating the organisms for high-resolution imaging.

BRIEF DESCRIPTION OF THE DRAWINGS

The patent file contains at least one drawing executed in color. Copies of this patent with color drawing(s) will be provided by the Patent and Trademark Office upon request and payment of the necessary fee.

Some embodiments of the present invention will now be explained, with reference to the accompanied drawings, in which.

The patent of application file contains at least one drawing executed in color. Copies of this patent or patent application publication with color drawing(s) will be provide by the Office upon request and payment of the necessary fee.

DETAILED DESCRIPTION OF PREFERRED EMBODIMENTS OF THE INVENTION

The present invention in a broadest sense is directed to systems and methods for use in, for example, studying reaction to drug treatment in a variety of specimen organisms, imaging of the specimen organisms, differentiating head and tail of the specimen organisms, providing optical or other stimulations to the specimen organisms, drug screening or genetic screening. In some specific aspects, the present invention is directed to systems and methods for use in automated vertebrate zebrafish larvae handling. Although the invention can be applied to different organisms, the following description focuses on using zebrafish larvae as a studying organism as an example. It is to be recognized that other teleosts and aquatic animals and embryos may be used and it is intended that other such specimen organisms be included within the term zebrafish larvae.

Figure 1:
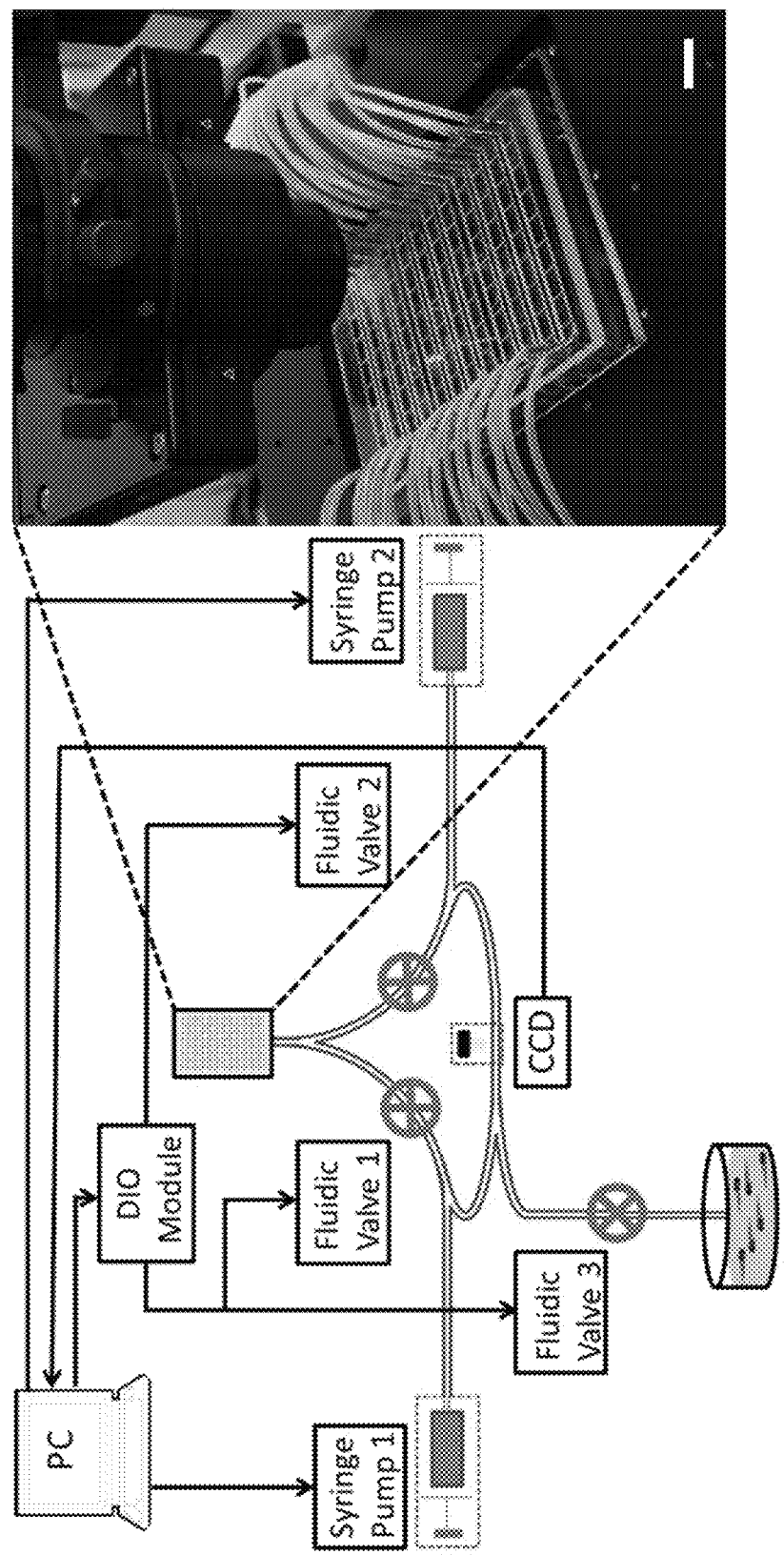
FIG. 1, including a schematic diagram (left) and a photographic image (right), shows an embodiment of a system with different control modules in accordance with the present invention.

The system allows automatic loading, positioning and orientating of multiple live and awake zebrafish larvae without using anesthetics or rigid gel, as shown in FIG. 1A syringe pump allows fish larvae to be loaded into the fluidic circuitry from a reservoir coupled with a fluidic valve.

Figure 2:
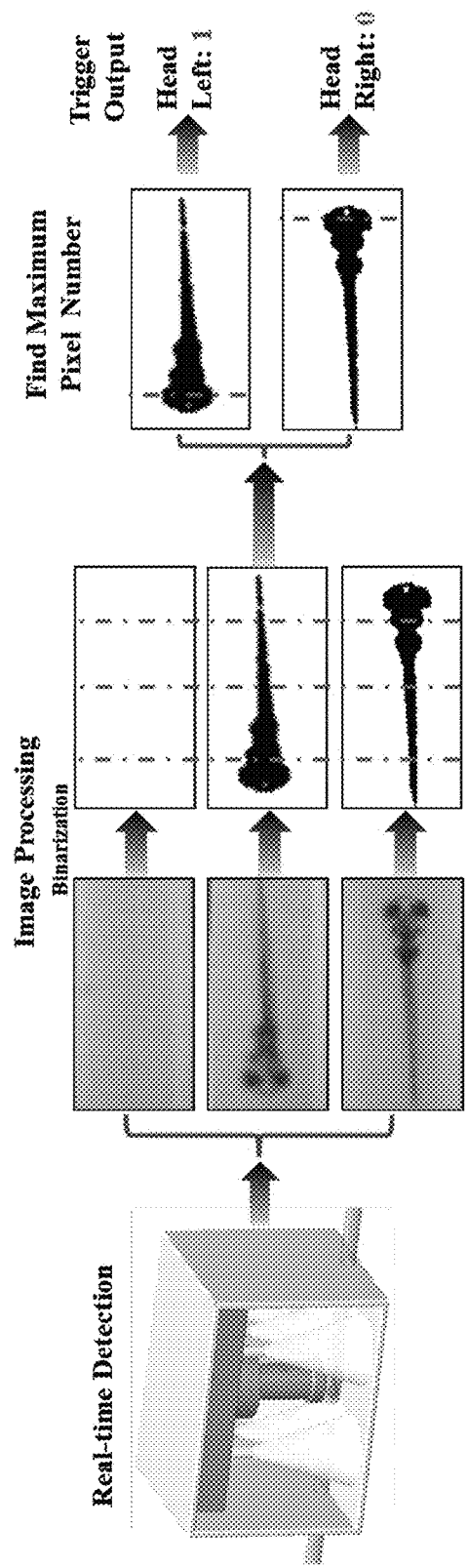
FIG. 2 is a series of schematic representations showing an embodiment of a detection module according to the present invention.

FIG. 2 shown the use of a detection unit configured to automatically discriminate the entry of larval zebrafish into the fluidic circuitry and may include two sets of LEDs and a camera. During fish detection, the camera would acquire real-time video of detection region. The image processing algorithm extracts each frame of this video and subsequently converts it to a binary image. Each image contains 160 pixel columns. It is assumed 3 detection pixel columns (namely m, n and r) and conduct the fish direction judgment only if $P(m)*P(n)*P(r)>0$. In the orientation judgment section, the algorithm would find the maximum pixel number $Q(s)$ among 160 pixel columns. If $s<80$, head left will be detected as a feed-back signal.

Figure 3:
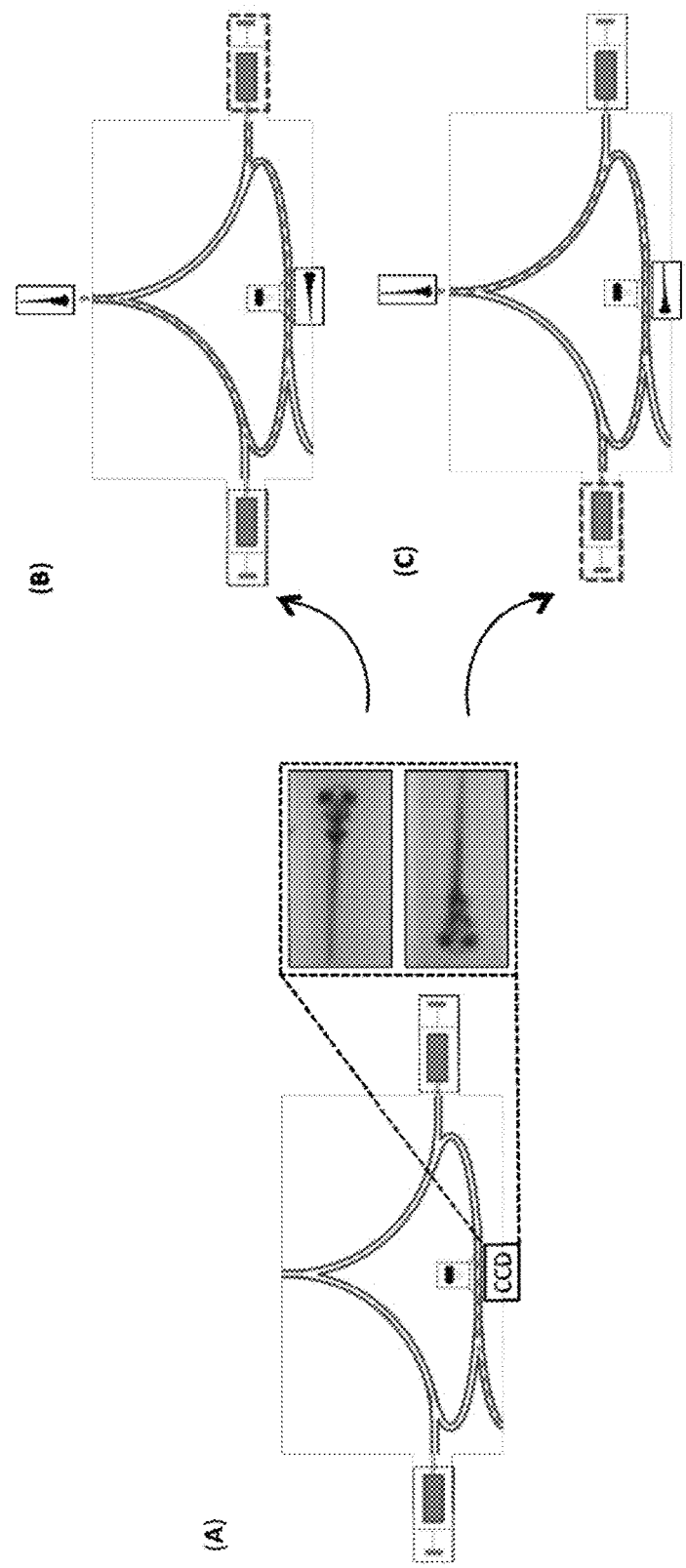
FIG. 3 includes diagrams (A), (B), and (C), showing an embodiment of a direction-switching-loop module of a system according to the present invention.

Portion A in FIG. 3 shows the detection unit which has successfully identified the loading and the head's direction of a larva aspirated from the reservoir and has activated a trigger. The trigger is outputted to perform the valve switching and pump activation in the direction-switching-loop module. For a larva loaded with head facing forward as shown in portion B of FIG. 3, the right pump (in red box) is engaged to pump the larva into next module. For a larva loaded with tail facing forward as shown portion C of FIG. 3, the left pump (in red box) is engaged to pump the larva into the Fish-Trap chip. As shown in portions B and C of FIG. 3, the actual flow direction indicated by the blue dash line.

Figure 4:
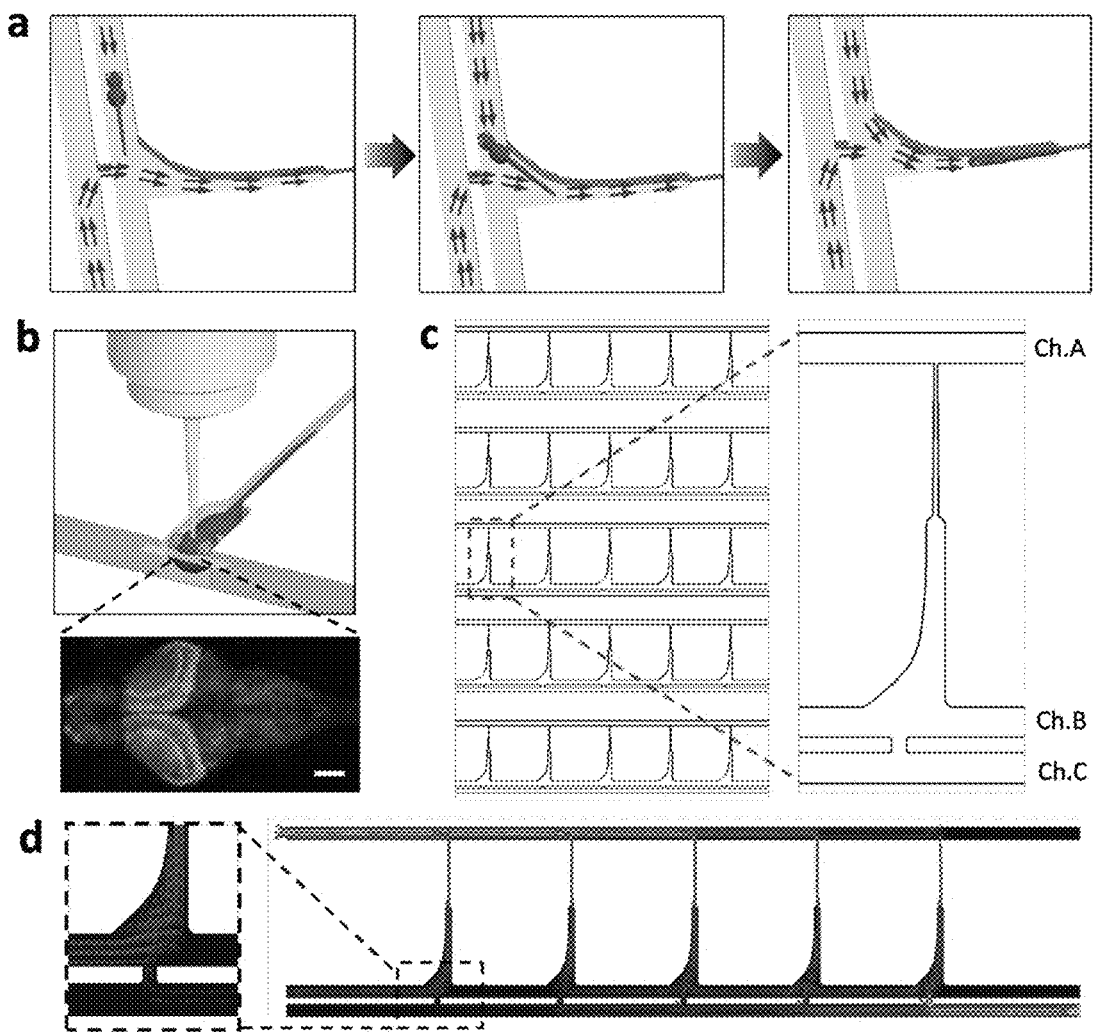
FIG. 4, including four sets of diagrams or photographic images, illustrates different aspects of an embodiment of a system in accordance with the present invention, the four sets of diagrams are labelled a, b, c and d, respectively.
Figure 5:
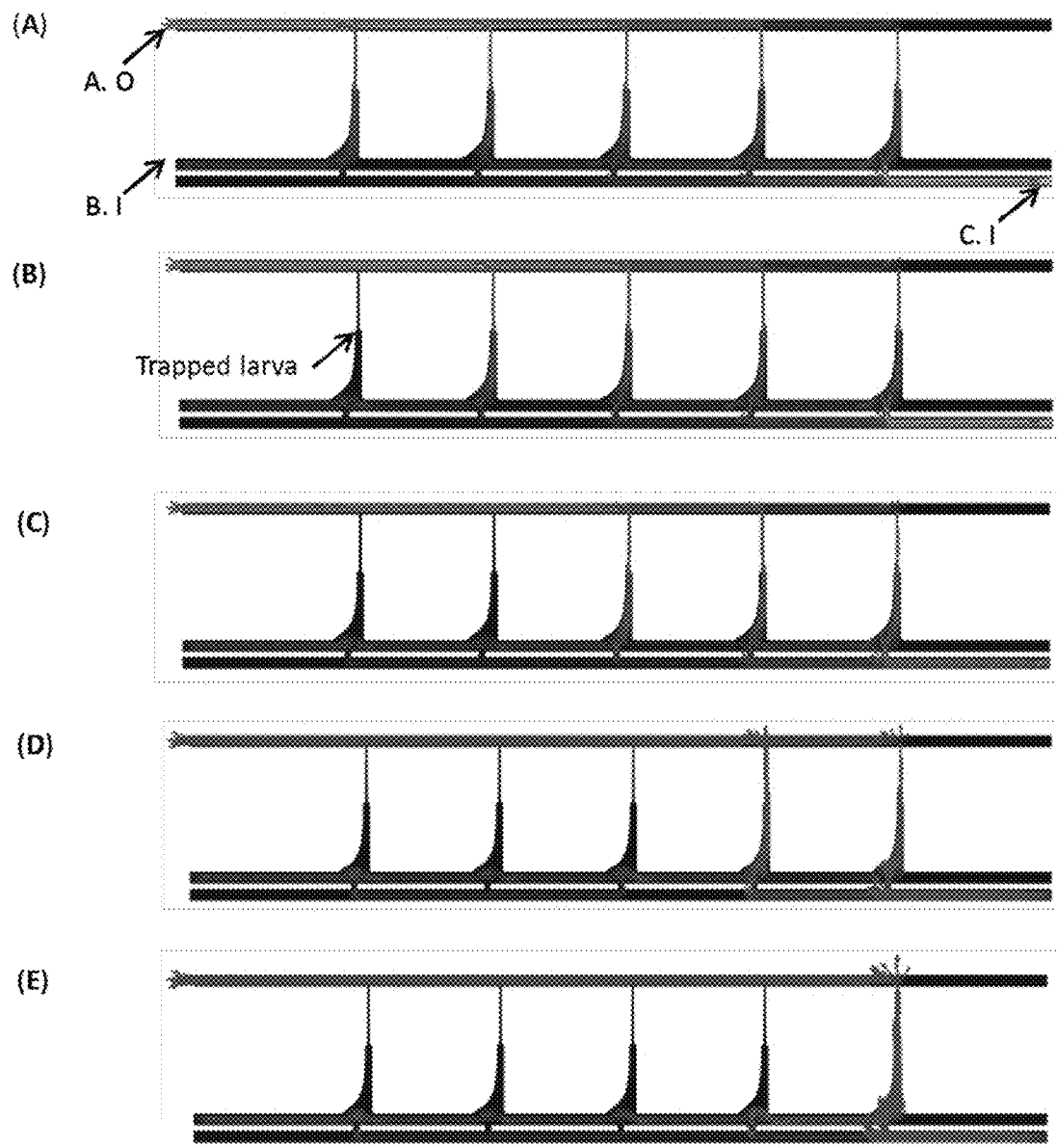
FIG. 5, including five sets of diagrams (A) to (E), shows simulation of sequential automatic trapping of subject organism using hydrodynamic force within an alternative microfluidic chip of a system.

FIG. 4 shows a key component of the trapping and orientating module, i.e. a microfluidic chip with specially designed channels that allow automatic trapping, positioning and orienting of multiple zebrafish larvae, even in live and awake status. The physical principle is to utilize hydrodynamic force to control the loading, trapping and positioning of single larva. Please see portions a, b, c and d in FIG. 4. Similar strategy can be used for reversible trapping of microbeads, cells, worm encapsulated droplets, and *drosophila* embryos in microfluidic devices. As illustrated in portion c of FIG. 4, the microfluidic chip is composed of two groups of horizontal flow channels, which are connected by series of trapping channels with tapering design mimicking the ergonomic structure of larval fish at specific developmental stages, mostly 4-6 days post fertilization (dpf) in an alternative embodiment. When a larva is loaded into horizontal channel B (Ch.B) with the tail facing forward, the bulk stream automatically carries it into the first trapping channel due to lower flow resistance. Please see portion d of FIG. 4. This trapped larva then acts as a plug, dramatically increasing the flow resistance and redirecting the main flow to other channels. Subsequent larva then bypass the occupied trapping channel, and is carried into a next trapping channel as shown in FIG. 5. Horizontal Ch.B is connected with channel C (Ch.C) through series of short vertical channels, through which fish water is continuously pumped into Ch.B to increase the hydrodynamic flow focusing into each of the trapping channels, as shown by the numerical simulation. Please see portions A and D in FIG. 5. One side of the inlet is designed to be curved to guarantee smooth sliding and to prevent potential damage to the larva due to sharp edges. The rear end of the trapping channel has a tapering design with a narrow restricted portion, which can only fit the tail of a larva. This feature is particularly important for robust immobilization and orientation of zebrafish larvae. After a larva was trapped, a 15 ml/h flow was continuously applied through Ch.B to maintain a slightly positive pressure in the device, so that the trapped larvae are secured in position for advanced microscopic imaging. Please see portion b of FIG. 4.

Figure 6:
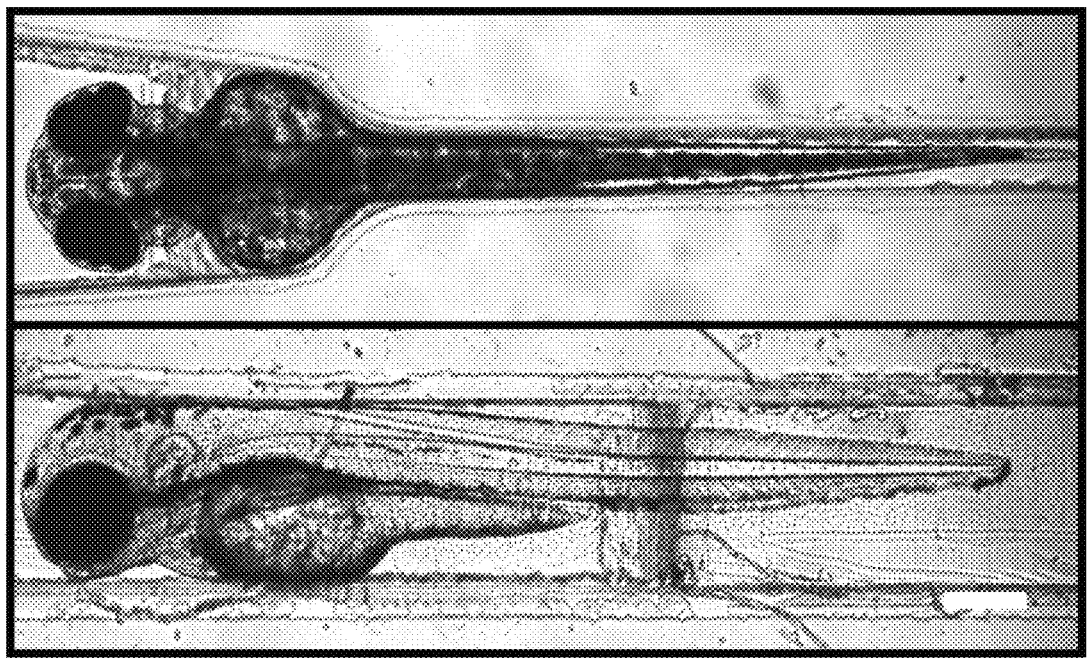
FIG. 6, including bright-field images of larvae trapped with different alternative microfluidic chips for dorsal/lateral orientation control.

With the use of the system, the larvae can be manipulated to adopt one of two major orientations: lateral or dorsal, thus rendering the capability to image different organs. In the research and studies leading to the present invention, it has been demonstrated that larva immobilization can be achieved in two types of trapping chips. Please see FIG. 6. The top image shows a larva oriented with a dorsal-chip and the bottom image shows a larva oriented with a lateral-chip. Scale bar, 200 µm. In this way, most major organ systems, such as brain, heart, liver, vascular structures, etc. can be optically accessed by using this system.

Figure 7:
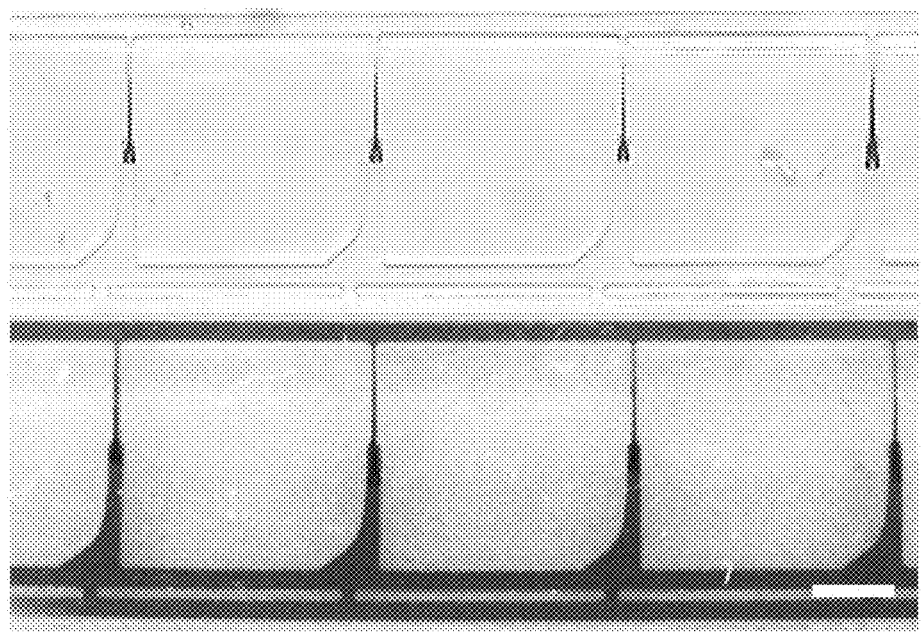
FIG. 7 includes images showing an embodiment of in situ drug treatment to multiple animals in the system.
Figure 8:
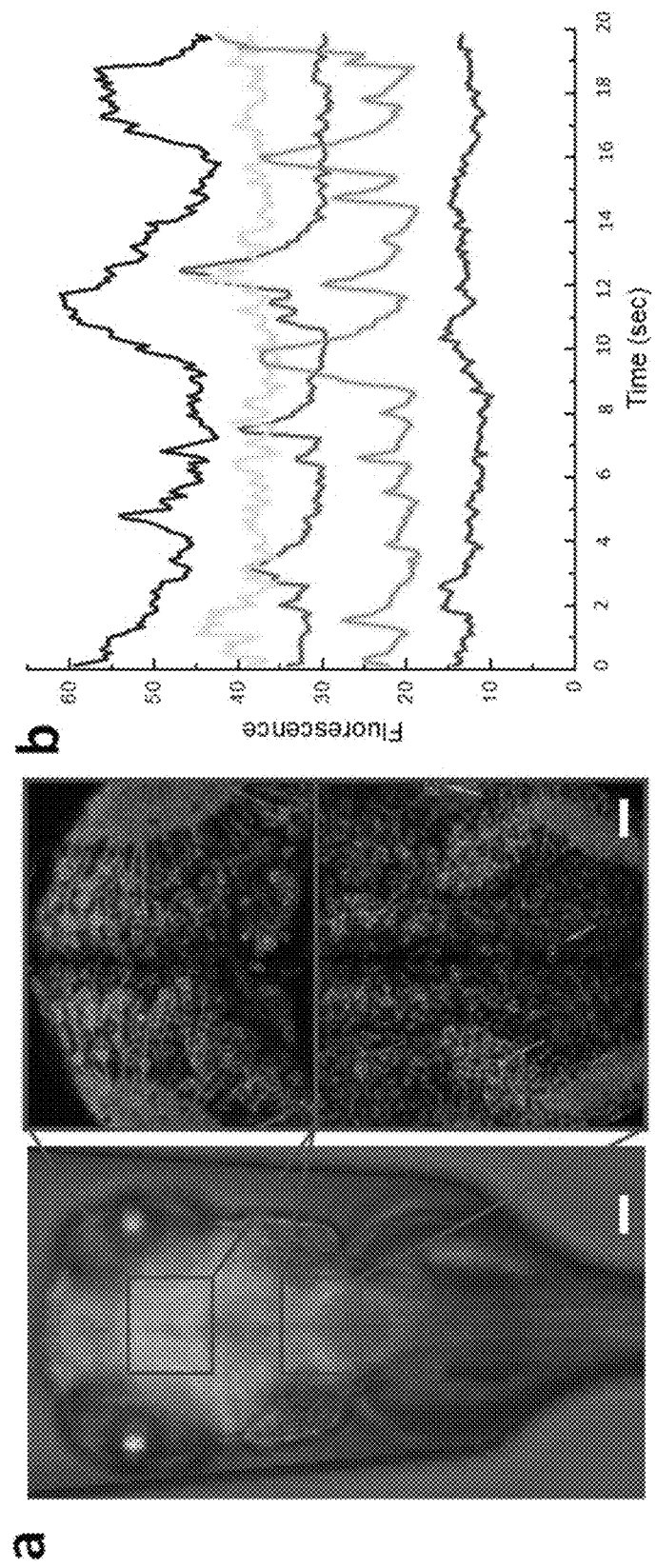
FIG. 8, including two sets of photographic images and graph, shows recording of brain-wide neural activity using the system of FIG. 1, the two sets of diagrams are labelled A and B in FIG. 2, respectively.

FIG. 7 shows that this system has the capability to expose the organisms to a compound or a drug to image acute effects. The scale bar is 2 mm. The compounds, drugs or therapeutic reagents were applied in situ by simple perfusion, and their acute or long-term effects on different organs, including the brain, were evaluated in real-time with single cell resolution. FIG. 8 shows an example how the system would be used to analyze brain-wide activity in larval zebrafish using the elavl3:GCaMP5G transgenic line. All neurons in these fishes were genetically encoded with calcium indicator, thus enabling direct monitoring of the spiking-induced calcium dynamics by fluorescence microscopy. When immobilized within the microfluidic chip, the calcium fluorescent signal from the entire brain can be reliably recorded with noticeable cell features. Please see portion a) in FIG. 8 in particular. Using confocal microscope with a tandem scanner, neural activity from specific brain regions can be recorded with single cell resolution with a 10 Hz frame rate. Please see portion b) in FIG. 8 in particular.

Figure 9:
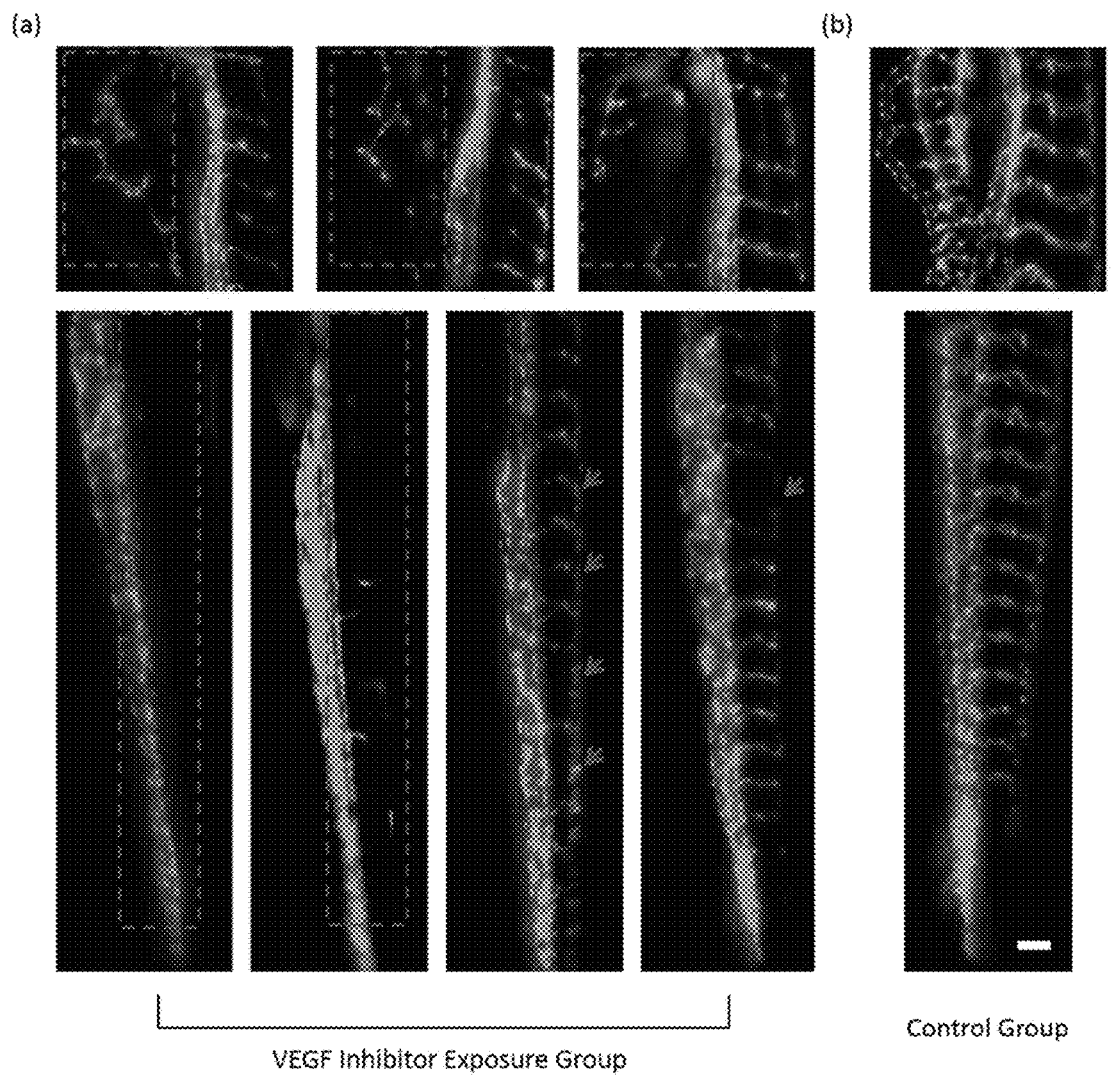
FIG. 9, including two sets of photographic images, namely A (test group) and B (control group), shows long term observation of organisms using an embodiment of a lateral chip according to the present invention.

For long-term observation, live imaging is also demonstrated in larvae immobilized with our system for 36 hours as shown in FIG. 9. In the testing group, Fli1 transgenic zebrafish larvae are exposed with VEGFR inhibitor for 36 hours. The VEGFR inhibitor concentration is 1 µM. In the control group, Fli1 transgenic zebrafish larvae are just incubated in the E3 water. The scale bar is 50 µm.

Figure 10:
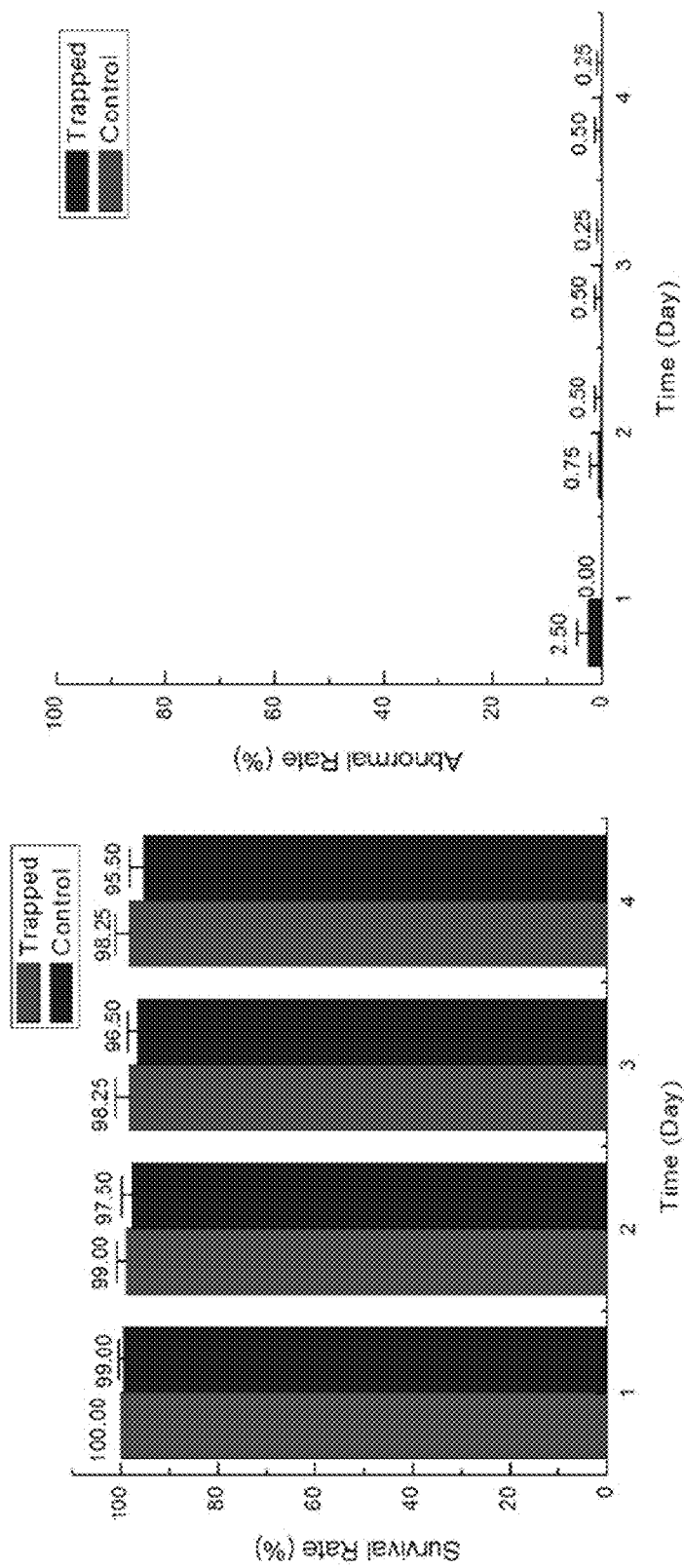
FIG. 10 includes illustrations showing a quantitative assessment of animal health handled in the system.

After running through a complete experimental cycle in the system, larvae are released from the system without any detectable injury. Please see FIG. 10. Practically, the system enabled proper loading with a success rate of 96.2% (n=500) for lateral chips or 94.80% (n=500) dorsal chips, respectively. It takes on an average 23.17±2.09 seconds (n=200) to process a single larva.

The above has demonstrated a high-throughput system for automatically immobilization and orientation of live and awake larval zebrafish, which enables single-cell-resolution imaging of specific organs in behaving and drug-responsive larvae without using anesthetics or rigid gel. The system can however be used, for example, in large-scale in vivo studies of complex processes such as cardiovascular and nervous system functions. Screening hundreds of animals demonstrates that the system works noninvasively and in a high success rate of orientation control. Thus, the system can dramatically improve the throughput and complex of unanaesthetic zebrafish screening.

It is envisaged that modifications and variations of the invention will be apparent to those of ordinary skill in the art, and it is intended that all such modifications and variations be included within the scope of the appended claims.

The invention claimed is:

1. An array-based high-throughput system for automated screening of live specimen organisms of teleost larvae comprising a head portion at one end and a tail portion at an opposite end, comprising:
   a. a first module for automatically trapping the organisms in desired positions for imaging purpose;
   b. a second module for automatically orienting the organisms with desired angles for imaging purpose;
   c. a third module for automatically and hydro-dynamically controlling head-to-tail direction of the organisms leaving a reservoir and firstly entering said trapping module and then said orienting module, wherein said third automatic head-to-tail controlling module includes a detection unit and a valve unit for discriminating and switching head-to-tail direction of the specimen organisms in a fluidic circuitry; and
   d. a fourth module for automatically loading the organisms from the reservoir into said direction control or trapping module;

wherein said trapping and orienting modules include an array of channels to allow hydro-dynamic flow of fluid carrying the organisms in said system; and wherein said array of channels include:
  i) a first conduit arranged generally horizontally and to which the oriented organisms are introduced;
  ii) one or more second conduits arranged generally vertically or perpendicularly with respect to said first conduit, said second conduit or conduits connected to and branched off from said first conduit; and
  iii) a third conduit arranged adjacent to and connected to said first conduit by one or more shunts, said third conduit allowing fluid exiting said third conduit to said first conduit via said shunt or shunts, said shunt or shunts is or are positioned next to respective entrance of the second conduit or conduits whereby hydro-dynamic fluid flow from said third conduit to the first conduit via said shunt or shunts at the entrance deflects fluid flow in said first conduit to said second conduit or second conduits for effecting trapping of one or more of the organisms in the second conduit or conduits; and
  iv) a fourth conduit connecting exits of the second conduits.

2. A system as claimed in claim 1, wherein the teleost larvae are at a development stage of 2-8 days of post fertilization.

3. A system as claimed in claim 1, comprising a plurality of pairs of said second conduits and corresponding said shunt, wherein said plurality of pairs of said second conduits and said shunts, the first conduit and the third conduit together form a capillary circuitry.

4. An apparatus as claimed in claim 1, wherein the fluidic circuitry is a loop capillary fluid circuitry.

5. An apparatus as claimed in claim 1, wherein said detection unit is a photo-detection unit including an LED illuminator, a camera to acquire real-time video, and an image processing algorithm to identify head or tail of the specimen organisms leaving said reservoir for said first conduit.

6. A system as claimed in claim 1, wherein each said second conduit resembles an elongate funnel structure having an enlarged portion at an inlet end, a restricted portion at an outlet end opposite to the inlet end, and a neck portion there between.

7. A system as claimed in claim 6, wherein said enlarged inlet portion transitions to said restricted outlet portion sharply at said neck portion, wherein said neck portion has an internal width of substantially 150 μm configured to trap a zebrafish larva in its lateral orientation.

8. A system as claimed in claim 1, wherein said second conduit with a height of substantially 500 μm is configured to trap a zebrafish larva in its dorsal orientation.

9. A system as claimed in claim 1, wherein said first conduit having an inlet and an outlet, and is subjected to a positive fluid pressure in operation.

10. A system as claimed in claim 1, comprising an optical, acoustic, thermal, hydrodynamic, chemical or pharmaceutical stimulator to provide a stimulus to the specimen organism trapped in the arrays of said second conduits.

11. A system as claimed in claim 1, wherein the fluidic conduits are made of essentially a transparent material suitable for optical observation or coupling.

12. A system as claimed in claim 1, wherein the system is free of using anesthetic reagents for immobilizing or orienting the specimen organisms.

13. A system as claimed in claim 1, wherein an imaging apparatus can be directly coupled to provide microscopic observation to the specimen organisms.

14. A system as claimed in claim 13, wherein the imaging apparatus has conventional, confocal, two-photon, wide-field and/or light sheet imaging capability.

15. A system as claimed in claim 1, comprising at least one syringe pump for loading larvae into a capillary fluidic circuitry and one or more fluidic valves for controlling operation state in said conduits.

16. A system as claimed in claim 15, wherein said syringe pump is coupled with said direction control module and said fluid valve(s).

17. A system as claimed in claim 1, comprising a computer unit for controlling flow rate in said first, second and third conduits, and performing automated control of larva loading cycles.

18. A system as claimed in claim 1, comprising a plurality of said second conduits arranged in sequence or in parallel for trapping and orienting respective plurality of organisms in an array format for sequential or parallel observation.

19. A system as claimed in claim 1, comprising means to release the specimen organisms trapped in said conduits by reversing flow direction of fluid in the conduits.

20. A method of high-throughput screening of subject whole specimen organisms with a head portion and a tail portion, comprising:
  a. automatically loading the organisms from a reservoir into a fluidic circuitry;
  b. automatically differentiating and hydro-dynamically switching head-to-tail direction of the organisms;
  c. automatically trapping and positioning the organisms in a desired orientation in an array format; and
  d. automatically orienting the organisms with desired angles;
  wherein the fluidic circuitry includes:
    i) a first conduit arranged generally horizontally and to which the oriented organisms are introduced;
    ii) one or more second conduits arranged generally vertically or perpendicularly with respect to said first conduit, said second conduit or conduits connected to and branched off from said first conduit, wherein the second conduits are sized and shaped to trap one or more of the organisms;
    iii) a third conduit arranged adjacent to and connected to said first conduit, said third conduit adapted such that fluid exiting said third conduit to said first conduit via a shunt or a plurality of shunts, said shunt or shunts connect said third and first conduits and is or are positioned next to respective entrance of the second conduit or conduits whereby fluid flow from said third conduit to the first conduit via said shunt or shunts at the entrance deflects fluid flow in said first conduit to said second conduit or second conduits; and
    iv) a fourth conduit connecting exits of the second conduits.

* * * * *